United States Patent [19]

Nathan et al.

[11] Patent Number: 4,563,350
[45] Date of Patent: Jan. 7, 1986

[54] INDUCTIVE COLLAGEN BASED BONE REPAIR PREPARATIONS

[75] Inventors: Ranga Nathan, Newark; Saied Seyedin, Mountain View; Karl Piez, Menlo Park; Hanne Bentz, Palo Alto, all of Calif.

[73] Assignee: Collagen Corporation, Palo Alto, Calif.

[21] Appl. No.: 664,158

[22] Filed: Oct. 24, 1984

[51] Int. Cl.⁴ .............................................. A61K 35/32
[52] U.S. Cl. ...................................... 424/95; 106/161; 260/123.7; 424/15; 514/21; 514/801
[58] Field of Search ........................ 260/112 R, 123.7; 424/95, 15; 106/161; 514/21, 801

[56] References Cited

U.S. PATENT DOCUMENTS

| | | | |
|---|---|---|---|
| 4,294,753 | 10/1981 | Urist | 260/112 R |
| 4,314,380 | 2/1982 | Miyata et al. | 3/1.9 |
| 4,394,370 | 7/1983 | Jefferies | 260/123.7 X |
| 4,407,787 | 10/1983 | Stemberger | 106/161 X |
| 4,430,760 | 2/1984 | Smestad | 3/1.9 |
| 4,434,094 | 2/1984 | Seyedin et al. | 260/112 R |
| 4,440,750 | 4/1984 | Glowacki et al. | 424/95 |
| 4,485,097 | 11/1984 | Bell | 424/95 |
| 4,488,911 | 12/1984 | Luck et al. | 106/161 |

OTHER PUBLICATIONS

Clin. Orthop. Rel. Res. (1982), Urist et al., pp. 219–232, 162.
Science, 220, (1983), 680–686, Urist et al.
Proc.-Natl.-Acad. Sci. USA, Nov. 1983, 6591–6595, Sampath et al.
Journal of Cell Biology, vol. 97, Dec. 1983, 1950–1953, Seyedin et al.
Proc.-Natl.-Acad.-Sci. USA, Jan. 1984, 371–375, Urist et al.
J. Biol. Chem., Oct. 25, 1981, pp. 10403–10408, Termine et al.
Cell. vol. 29, 99–105, 1981, Termine et al.

Primary Examiner—Howard E. Schain
Attorney, Agent, or Firm—Ciotti & Murashige

[57] ABSTRACT

A composition suitable for inductive bone implants is disclosed. The composition comprises a purified form of osteogenic factor in admixture with an carrier having a percentage of non-fibrillar collagen. The resulting implants are sufficiently hypo-immunogenic to be effective when implanted in xenogeneic hosts.

14 Claims, 5 Drawing Figures

INDUCTIVE COLLAGEN BASED BONE REPAIR PREPARATIONS

TECHNICAL FIELD

The present invention relates to bone repair materials. More specifically, it relates to non-fibrillar collagen supports for chondrogenic/osteogenic proteins.

BACKGROUND ART

Repair of damaged or defective bone which involves more than the healing of a simple fracture has used three approaches to supply the required bone tissue: In the simplest approach, a prosthesis, intended to be permanent, is placed as a substitute for missing bone, and provisions made to integrate the prosthesis into the skeletal structure of the host. Such bone replacements may be made of artificial materials such as biocompatible metals, or may constitute allografts derived from bone structure elsewhere in the subject. A slightly more complex approach has been to provide a matrix to support ingrowth of bone from surrounding healthy tissue with subsequent possible resorption of the matrix. A third approach has been to supply both a matrix and an osteogenic factor which biochemically induces the ingrowth with or without a cartilagenous intermediate.

The history of development of the last two approaches, often called, respectively, "conductive" and "inductive" repair, shows continuing progress toward biologically derived materials which are of sufficiently low immunogenicity to enable them to function without unfavorable side effects. Since collagen is the major organic component of bone, its use as, or in, a matrix for subsequent deposit of the mineral bone component by adjacent cells has been extensive. However, collagen per se contains "telopeptide" units which are immunogenic, and a great improvement with respect to collagen for use in such matrix construction has been the use of "atelopeptide" collagen. Removal or partial removal of the telopeptides and consequent suppression of the immunogenic response may be important as this improves the performance in conductive bone repair of collagen derived from species foreign to that of the host—i.e., using "xenogeneic" collagen. For human recipients, this is significant because porcine, bovine, or other mammalian sources may be used for the preparation, rather than cadavers or related human donors, thus providing a much more inexpensive and plentiful source of supply. On the other hand, atelopeptide—containing collagen may also be useful in some instances.

Incompatibility problems are increased when inductive implants are used, as not only does the matrix need to be acceptably compatible with the host, but also the preparation of any factors which induce cartilage and bone formation. In earlier work, demineralized bone (DMB) was used as part of the implant preparation in order to provide a source of such factors. See, for example, U.S. Pat. Nos. 4,440,750 and 4,430,760 and U.S. Ser. No. 411,659 filed Aug. 26, 1982. Various attempts have been made to purify, from bone, the factors, presumably protein, which are responsible for osteoinduction. U.S. Pat. Nos. 4,294,753 and 4,455,256 to Urist disclose a bone morphogenic protein (BMP) which is extracted from demineralized bone using urea or guanidine chloride, and then reprecipitated. Further purifications of this factor have been reported by Urist in *Clin Orthop Rel Res* (1982) 162:219; *Science* (1983) 220:680; and *Proc Natl Acad Sci* (USA) (1984) 81:371. The BMP reported by Urist has a molecular weight of 17,500-18,000 daltons and is unadsorbed to carboxymethyl cellulose (CMC) at pH 4.8.

Presumptively different osteogenic factor (OF) proteins were isolated from DMB and purified by Seyedin and Thomas (U.S. Pat. No. 4,434,094 and Ser. No. 630,938, filed July 16, 1984, and assigned to the same assignee). These preparations indicated a molecular weight of approximately 26,000 daltons for a factor which, unlike the Urist factor, is adsorbed to CMC at pH 4.8. This factor was sufficiently purified that it was not immunogenic in xenogeneic hosts.

Attempts have been made to combine sources of an osteoinductive factor with a biocompatible support. U.S. Pat. No. 4,440,750 (supra) discloses a reconstituted atelopeptide collagen preparation in combination with DMB, or a DMB extract. U.S. Pat. No. 4,394,370 to Jeffries discloses the combination of a collagen preparation (which, however, contains the telopeptides); and a crude extract of DMB. The Jeffries disclosure while commenting that "BMP" is not species specific in its activity, exemplifies the use only of allogenic DMB as the starting material for the extract, presumably because of perceived problems with immunogenicity. Also, the Jeffries disclosure requires the use of a miniumim of 5% DMB extract by weight in the compositions. The combination with collagen support was apparently not tested in vivo. Reddi, et al, *Proc Natl Acad Sci* (1983) 69:1601 described the use of allogenic demineralized bone powder to evoke cartilage and bone formation in rat hosts. Sampath, T. K. et al (*Proc. Natl Acad Sci* (USA (1983) 80:6591–6595)) have also suggested the combination of allogenic rat bone collagen powder (presumably lacking the osteogenic factor) and a low molecular weight osteogenesis factor (presumably that of Urist) to be effective in bone repair in rat subjects. Thus, while the osteogenesis factor was xenogenic, the support provided by the conductive portion of the implant disclosed in the Sampath (supra) was allogenic.

Because of supply and cost considerations, it would be advantageous to provide an entirely xenogeneic osteoinductive support implant. In order to do this, it is necessary to provide a support with the effective disposition of a OF protein, wherein both the support and OF protein are of acceptably low immunogenicity.

DISCLOSURE OF THE INVENTION

The invention provides an implantable material for inductive bone repair which contains both a chemically defined hypo-immunogenic supporting matrix for bone growth and an effective amount of a purified osteoinductive factor which biochemically promotes the ingrowth of bone. The intermediate formation of cartilagenous tissue may also occur. The compositions of the invention can be utilized for repair of major and minor bone defects whether used for reconstruction, onlays, or for peridontal purposes.

Thus, in one aspect, the invention comprises a composition effective in inducing and supporting bone growth in a subject mammal which composition comprises an osteoinductively effective amount of a chondrogenic/osteogenic (OF) protein derived from bone sufficiently free from impurities so as to be hypoimmunogenic, in combination with carrier preparation containing at least 5%, but preferably at least 10% nonfibrillar collagen. The remaining (supplemental) portion of the carrier preparation can be any biocompatible material, such as fibrillar collagen, hydroxyapatite, tricalcium phosphate or mixtures thereof.

The OF will ordinarily be present in the amount of about 1-1000 ppm of pure OF based on the total composition; the preparations of OF used to prepare the composition are sufficiently pure that a maximum of 2% wt/wt of OF preparation is added.

In other aspects, the invention relates to methods of effecting bone repair in subject mammals by implantation of the compositions of the invention.

MODES OF CARRYING OUT THE INVENTION

A. Definitions

As used herein, "osteoinductive" and "osteogenic" are used interchangeably and refer to conversion of bone progenitor cells into living osseous tissue. The induction may result in osteogenesis—i.e., direct formation of mineralized bone through secretion of the organic and inorganic components of bone, or the osteoinduction may also involve intermediate formation of cartilage—i.e., the osteoinductive factor may also be chondrogenic. Indeed, proteoglycan which is diagnostic for cartilage formation, is used as an index of osteoinductive activity of the compositions of the invention.

"Derived from" when referred to the osteogenic factors herein refers to a structural relationship or homology. It is not limited to physical derivation. Thus osteogenic factor "derived from" bone indicates that the factor or factors has an amino acid sequence homologous and similarly functional to those of factors natively produced in bone tissue; it does not necessarily mean that the material used is directly isolated from bone per se. It might, for example, be made synthetically, or by using recombinant DNA techniques.

"Hypo-immunogenic" refers to an acceptable biocompatibility. It is understood that many substances may be immunogenic in some animals and applications but are not able to raise detectable levels of specific immunogoloblins in others. It is also understood that complete absence of specific immunoglobins and of inflammation may not be required. Thus, when used to describe the composition components or the compositions of the invention, "hypo-immunogenic" is functionally defined to mean that any immune responses are within acceptable levels.

"Atelopeptide collagen" refers to collagen which has been suitably treated so as to remove or partially remove the telopeptide, or immunogenic portions. Briefly, and in explanation, collagen comprises a fibrillar structure composed of bundles of triple helical configurations of repeating amino acid sequences. These triple helical sequences are terminated by non-helical structures, "telopeptides" which are responsible both for the cross-linking between various collagen chains, and, in part, for the immunogenicity of collagen preparations. Removal of these structures can be accomplished by treating with suitable proteolytic enzymes such as trypsin. The resulting atelopeptide collagen is more suitable for xenogeneic use, as the major species-specific immunogens have thus been removed.

"Non-fibrillar collagen" has been treated so as not to maintain its native fibrillar structure. This term thus refers to collagen which has been solubilized and has not been reconstituted into its native fibrillar form. The fibrillar construction can be disrupted by dissolution; it can be returned to solid form either by reconstituting the fibers (fibrillar) or by non-specific aggregation (non-fibrillar). Non-fibrillar collagen can also be prepared by denaturation e.g. by heating the fibers with or without first solubilizing them.

The non-fibrillar collagen useful in the invention is used as a solution, as a gel, or as a solid which is non-specifically aggregated after dissolution such as through lyophilization. It must not be reconstituted—i.e., it must not be returned to fibrillar form.

Percentages of OF in the compositions of the invention are given in terms of the pure osteoinductive protein used, not of the crude preparation. As will be clear from the discussion below, the availability of techniques for purification of OF protein to homogeneity permit establishing a relationship between mg of protein and units of activity. Thus, even a relatively impure preparation may be assessed as to mg OF present by assay of its activity, and an amount of the preparation which will provide a desired weight of pure protein calculated.

B. General Description

The compositions of the invention are mixtures of effective amounts of an osteoinductive factor (OF) preparation which is sufficiently purified to be hypo-immunogenic when used xenogeneically, with carrier preparation containing at least 5% but preferably at least 10% of its weight as a non-fibrillar collagen preparation. The percentage of a particular OF preparation needed in the composition will, of course, depend on the purity of the preparation.

Proteins exhibiting osteoinductive activity have been purified to homogeneity, as set forth in U.S. Ser. No. 630,938 filed July 16, 1984 and assigned to the same assignee. Effective levels can thus rationally be calculated in terms of the content of this pure material, rather than an amount of crude extract. Indeed, as referred to herein, the description of the compositions is cast in terms of pure factor. The compositions will thus be nearly entirely the collagen matrix for pure preparations of OF, i.e., they will contain about 1-1000 ppm of the OF protein. However if less pure preparations of OF are used, up to 2% of the mixture may need to be made up of this preparation.

OF preparations which meet the criterion of sufficient purity to be hypo-immunogenic in xenogeneic hosts may be prepared in several ways. As sources for the factor, bone, dentin, osteosarcomas, or chondrosarcomas and other tissues of vertebrate origin containing OF can be used. It has been shown that OF preparations from human, monkey, bovine and rat are non-species specific in their ability to produce endrochondreal bone in xenogeneic implants by Sampath, T. K., et al, *Proc.*

*Natl Acad Sci* (USA) (1983) 80:6591. Thus the OF which is usable in the mixtures of the invention may derive from any of these sources, and, indeed, may be any protein having osteoinductive activity which is substantially similar to those proteins derived from vertebrate sources, whether thus prepared, modified by inadvertent or intentional means, prepared by chemical synthesis, recombinant DNA techniques, or other such procedures. For example, in addition, the bone morphogenic protein of Urist, if purified sufficiently, could also be used. The OF must meet the requirements only of substantial similarity to a protein derivable from a vertebrate source, osteoinductive functionality, and acceptably low immunogenicity.

One useful process for preparing the OF useful in the compositions of the invention is set forth in U.S. Ser. No. 630,938 incorporated herein by reference. The methods therein disclosed result in homogeneous protein. Briefly, the method comprises treating porcine or bovine long bone materials (because of ready availability) with mechanical and abrasive techniques to clean and fragment them, and defatting by extraction with organic solvents such as ether or ethyl acetate, and then demineralizing usually by extraction with strong acid using standard techniques, and then using the resulting DMB as a starting material.

To isolate the factor, DMB is then extracted with a chaotropic agent such as guanidine hydrochloride (at least about 4M), urea (8M) plus salt or various other chaotropic agents. The extraction is preferably carried out at reduced temperatures in the presence of protease inhibitors to reduce the likelihood of digestion or denaturation of the extracted protein, for about 4 hr–1 day. After extraction, the extractant may be removed by suitable means such as dialysis against water, controlled electrophoresis, or molecular sieving or any other suitable means. The extract, with or without the extractant removed, is then subjected to gel filtration to obtain fractions of molecular weight below about 30,000 daltons using standard techniques. The low molecular weight fraction is freed from competing ions and is then subjected to ion exchange chromatography using CMC at approximately pH 4.5–5.2, preferably about 4.8 in the presence of a non-ionic chaotropic agent such as urea; other cation exchangers may also be used.

The active eluate fractions resulting from the cation exchange chromatography may be used directly in the compositions of the invention. They may also be further purified, if desired, by a reverse phase HPLC or non-denaturing gel electrophoresis. When either of these two techniques are applied to the eluate, homogeneous protein preparations are obtained.

Alternatively, the low molecular weight proteins obtained from the size separation as set forth above may be treated with an anion exchange resin such as DEAE cellulose, in the presence of, for example, 6M urea and 20 mM sodium phosphate at approximately pH 7.2. In this treatment, the non-adsorbed protein, after dialysis to remove urea may be used. The protein in the anion exchange resin treated solution can be recovered by lyophilization, or stabilized by dialyzing against 0.01N HCl. The OF-containing solution or solid from this method of preparation may also, if desired, be further purified; this is an optional step. Specific details of illustrative methods for thus purifying the OF proteins to a satisfactory level, are set forth below in paragraph C. In all cases, the fraction containing OF is sufficiently pure that no more than 2% wt/wt of factor preparation to collagen is used in the composition.

The carrier portion of the composition contains at least 5%, preferably at least 10% non-fibrillar collagen and, optionally, a supplemental component such as fibrillar collagen or ceramic or both.

The non-fibrillar collagen used can be supplied as a collagen in solution, as a lyophilized form of collagen in solution which is thereby non-specifically aggregated, as a gelatin carrier or as mixtures of the foregoing.

A preferred source of the non-fibrillar collagen is collagen in solution (CIS) which is obtainable under the trademark Zygen ® from Collagen Corporation, Palo Alto, Calif. However, any non-reconstituted collagen preparation may be used. This non-fibrillar portion must be present in an amount of at least approximately 5% in the composition. It may, however, constitute the entire collagen component of the composition. An attribute of the compositions of the invention is aceptably low immunogenicity. Accordingly it is preferable to use the atelopepetide form of collagen in all the preparations of this non-fibrillar collagen component. There may, however, be instances in which the presence of telopeptides, due to the configuration of the implanted composition, the susceptibility of the host, or some other reason, is not sufficiently detrimental to the hypoimmunogenicity to render the composition unacceptable. In other words, the use of atelopeptide non-fibrillar collagen is preferred, but not necessarily required.

The remaining material in the composition, if included, may be any biocompatible material, such as a fibrillar collagen preparation, a ceramic, or both. The fibrillar collagen can be derived from various sources, and a number of fibrillar collagen preparations are available in the art, wherein collagen derived from bone or skin of various mammals has been solubilized or dispersed in liquid medium and then recovered in fibrillar form. Preparations wherein the collagen is reconstituted into fibers include, for example, Zyderm ® collagen implant (ZCI), available from Collagen Corporation, Palo Alto, Calif. Other fibrillar preparations, include Avitene ®, which represents dispersed fibers that still have native fibrillar form; and Collagenfleece ® which is a dispersed preparation subsequently freeze dried. A preferred collagen is derived from bone, such as bone collagen powder (BCP).

A preparation of BCP is described in detail in U.S. Ser. No. 628,328, filed July 6, 1984 and assigned to the same assignee, incorporated herein by reference. Other collagen preparations which might be used, e.g., those that are reconstituted from non-bone sources, such as ZCI or lyophilized collagen gel may also be effective as acceptable fillers in admixture with the non-fibrillar component.

Non-collagenous components may also be used, either alone or together with collagenous supplements. For example, ceramic materials such as hydroxyapatite (HA) or other calcium phosphate preparations may be used. These materials have been disclosed to be useful in the construction of hard tissue implants and are thus of suitable biocompatibility to comprise a portion of the composition of the invention. See, e.g. U.S. Pat. No. 4,314,380 which discloses HA preparations, and Hayashi, K. et al *Arch Orthop Traumat Surg* (1982) 99:265 which discloses an alternate form of HA.

The compositions can also be used in conjunction with metal prostheses, such as those made of aluminium, or of alloys. U.S. Pat. No. 3,820,167, e.g., describes a prosthesis fabricated of titanium or an alloy thereof. The composition of the invention serves to close any gaps between the prosthesis and surrounding bone, and thus to secure the prothesis more firmly in place.

These additional components supplementing the required percentage of non-fibrillar collagen in the composition may be used singly, in admixture with each other, or not at all. They constitute as much as, but not more than 95% of the carrier portion of the final composition. Depending on the nature of these additional materials in the carrier and upon the mode of preparation, the properties of the composition can be varied to adapt to particular types of bone reconstruction or repair procedures. In a preferred composition for many applications, the carrier supplement contains fibrillar collagen, hydroxyapatite or mixtures thereof.

In one protocol suitable to prepare the mixtures which constitute the compositions of the invention, the non-fibrillar collagen is supplied as a solution, such as CIS, or as gelatin and is mixed, if desired with an additional component, such as for example, BCP or other biocompatible material. Certain ceramic materials, such as HA, however would dissolve in the subsequent step, and must be added after lyophilization (see below). The resulting mixture is mixed with the purified OF-containing preparation or with the pure protein and stirred in dilute mineral acid, e.g., 0.01N HCl, for 1–2 hr at low temperature, roughly 4° C. The mixture is then dialyzed against water at a pH below about 5 and lyophilized to obtain a solid material. The solid material may also be supplemented with additional compatible substances.

The physical properties of the resulting solid material are variable by appropriate modifications of the foregoing protocol and by adjusting the nature and amount of the supplemental carrier material. Thus the compositions may be in the form of powders, sheets, or rigid solid, such as a block or rod. The solid material can be formed into implants appropriate to uses in the repair of bones, either as onlay grafts, in bone reconstruction, in the treatment of fractures and in other orthopedic indications. The methods for utilizing solid compositions to form such implants, and surgical methods for implanting them, are well understood in the art, and the compositions of the invention are useful in employing these standard means.

When placed in the desired location, the implant composition provides a matrix for the ingrowth of new cartilage and bone, as well as stimulating the production of these materials by virtue of the presence of an osteoinductive factor.

As described in the specific examples below, these compositions when implanted subcutaneously in xenogeneic hosts, are capable of stimulating bone tissue formation. Their capacity to do so can be verified by explanting the composition, and assessing the explant histologically, for cartilage proteoglycan formation, for the presence of calcium and for the presence of alkaline phosphatase. In addition, the host organism is shown to be free from antibodies reactive against the implanted material.

EXAMPLES

The following examples are intended to illustrate the invention. Alternative methods for preparing the components of the composition and for preparing the composition itself are within the scope of the invention, provided the resulting composition falls within the scope of the appended claims.

C. Preparation of Osteoinductive Factor

C.1. Preliminary Extraction and Purification Steps

C.1.a–C.1.c are common to all exemplified preparations. The fraction F2 as set forth in paragraph C.1.c can then, be used in several alternative ways. First, it can be subjected to ion exchange chromatography as set forth in paragraph C.2 and the collected combined fractions having OF activity used as the OF preparation in the composition of the invention. Second, these fractions can be subjected to further purification representing either reverse phase HPLC as in paragraph C.3 or gel electrophoresis as set forth in C.4. Either of these further purified materials can also be used, and require lesser amounts of preparation to be utilized. Third, the material represented by fraction F2 in paragraph C.1.c may also be subjected to treatment with DEAE cellulose as set forth in paragraph C.5. After DEAE cellulose treatment, the non-adsorbed solution can be used in the compositions of the invention or this too can be further purified in a manner analogous to the carboxymethylcellulose (CMC) elutates. Thus, in general, according to the purification techniques illustrated in this paragraph, sufficient purification is obtained to provide suitable preparations by a combination of extraction with chaotropic agent, size-separation, and subsequent treatment with either DEAE or CMC. Further purification steps are then optional.

C.1.a. Preparation of Demineralized Bone (DMB)

Fresh bovine metatarsal bone was obtained from the slaughterhouse and transported on dry ice. The bones were cleaned of marrow and non-bone tissues, broken into fragments smaller than 1 cm diameter, and pulverized in a mill at 4° C. The pulverized bone was washed twice with 9.4 liters of double distilled water per kg of bone for about 15 min each wash, and then washed overnight in 0.01N HCl at 4° C. Washed bone was defatted using 3×3 volumes ethanol, followed by 3×3 volumes diethyl ether, each wash for 20 min, and all at room temperature. The resulting defatted bone powder was then demineralized in 0.5N HCl (25 l/kg defatted bone) at 4° C. The acid was decanted and the resulting DMB washed until the wash pH was greater than 4, and the DMB dried on a suction filter.

C.1.b. Extraction of Noncollagenous Proteins

The DMB was prepared in paragraph C.1.a was extracted with 3.3 liters of 4M guanidine-HCl, 10 mM ethylenediaminetetraacetic acid (EDTA), pH 6.8, 1 mM PMSF, 10 mM NEM per kg for 16 hr, the suspension suction filtered and the non-soluble material extracted again for 4 hr. The soluble fractions were combined and concentrated at least 5-fold by ultrafiltration using an Amicon ultrafiltration (10K) unit, and the concentrate dialyzed against 6 changes of 35 volumes cold deionized water over a period of 4 days, and then lyophilized. All of the procedures of this paragraph were conducted at 4° C. except the lyophilization which was conducted under standard lyophilization conditions. In some cases the concentrated extract from ultrafiltration was used directly in the gel filtration step of paragraph C.1.c.

C.1.c. Gel Filtration

Figure 1:
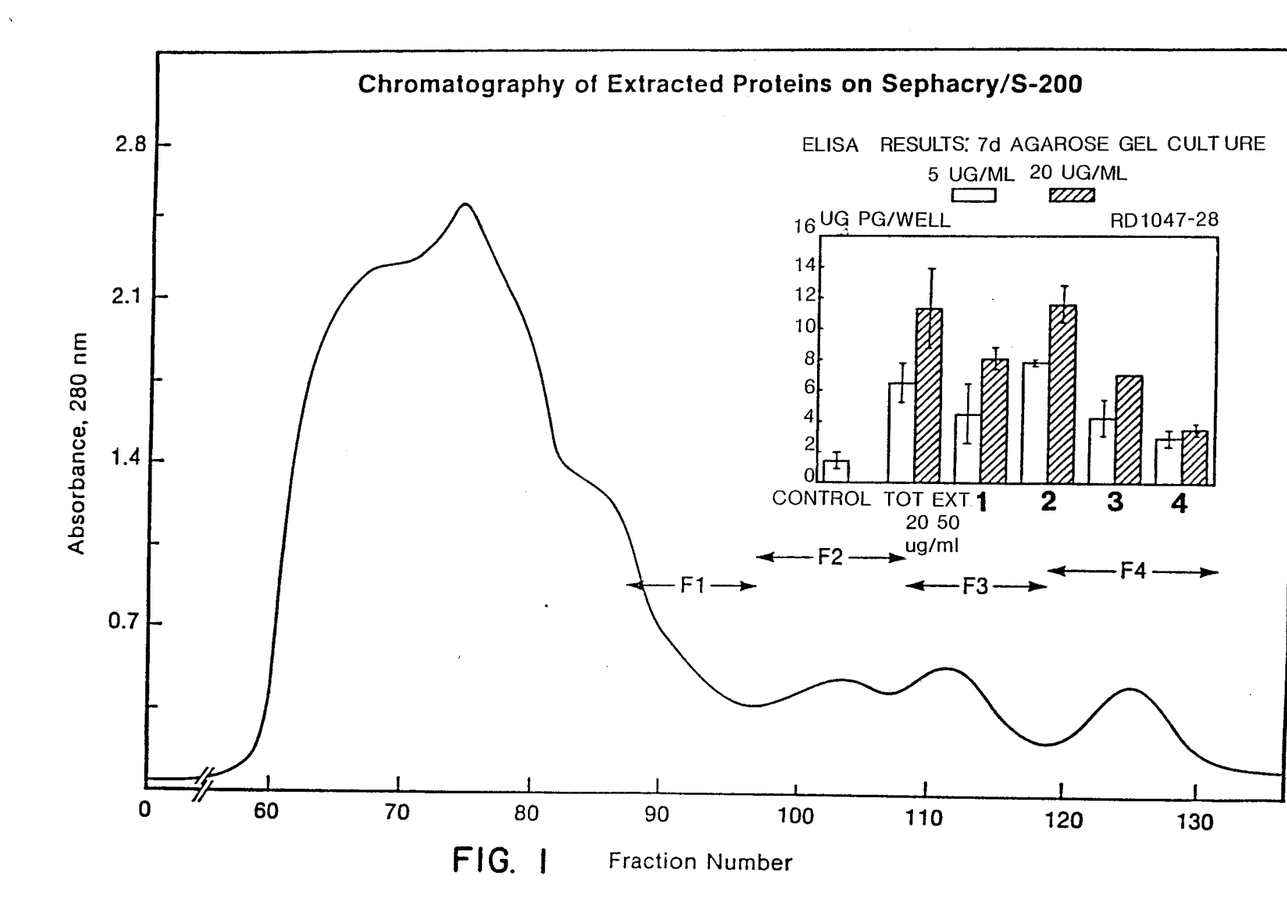
FIG. 1 shows the results of Sephacryl S-200 fractionation of a concentrated, resolubilized extract from DMB. Fraction F2, representing a MW range of 10,000-30,000 daltons contains the OF activity.

The ultrafiltration concentrated extract or the lyophilized material from paragraph C.1.b, redissolved in 4M guanidine-HCl, was fractionated on a Sephacryl S-200 column equilibrated in 4M guanidine-HCl, 0.02% sodium azide, 10 mM EDTA, pH 6.8. Fractions were assayed by their absorbance at 280 nm and for chondrogenic activity by ELISA (Seyedin et al. *J. Cell Biol* (1983) 97:1950) and the fractions were combined as shown in FIG. 1. Fraction F2 of FIG. 1, constituting a low molecular weight (LMW, 10,000-30,000 daltons) protein fraction possessing the greatest activity was dialyzed against 6 changes of 180 volumes of deionized water and lyophilized. All operations except lyophilization were conducted at room temperature.

C.2. Ion Exchange Chromatography

Figure 2:
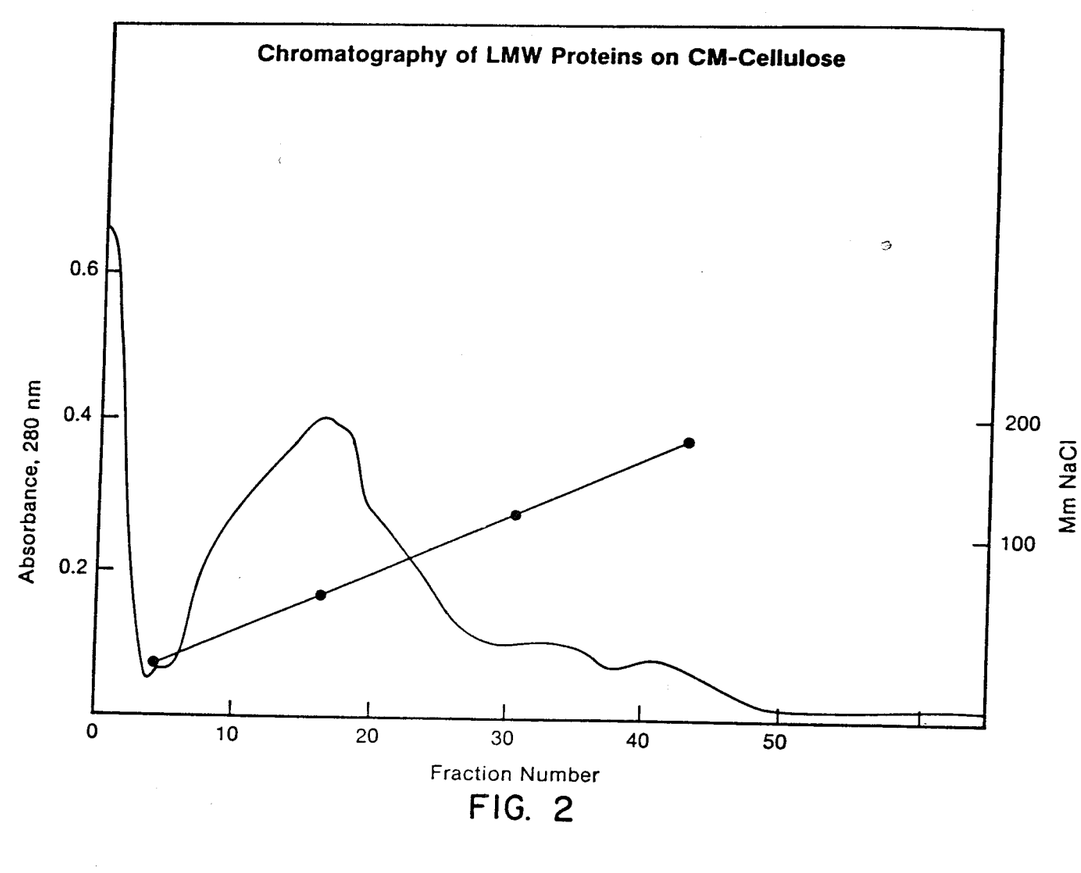
FIG. 2 shows the results of CMC fractionation of the F2 fraction of FIG. 1. The fraction eluting between 100-250 mM NaCl contains the OF activity.

Fraction F2 from paragraph C.1.c was dissolved in 6M urea, 10 mM NaCl, 1 mM NEM, 50 mM sodium acetate, pH 4.8 and centrifuged at 10,000 rpm for 5 min. The supernatant was fractionated on a CM52 (a commercially available CMC) column equilibrated in the same buffer. The column was eluted using a 10 mM to 400 mM NaCl gradient in the same buffer, and fractions collected and combined based on their absorbance at 280 nm as shown in FIG. 2. The eluate between 100-250 mM NaCl was dialyzed against 6 changes of 110 volumes of deionized water for 4 days and lyophilized. All of the foregoing operations were conducted at room temperature except dialysis (4° C.).

C.3. RP-HPLC

Figure 3:
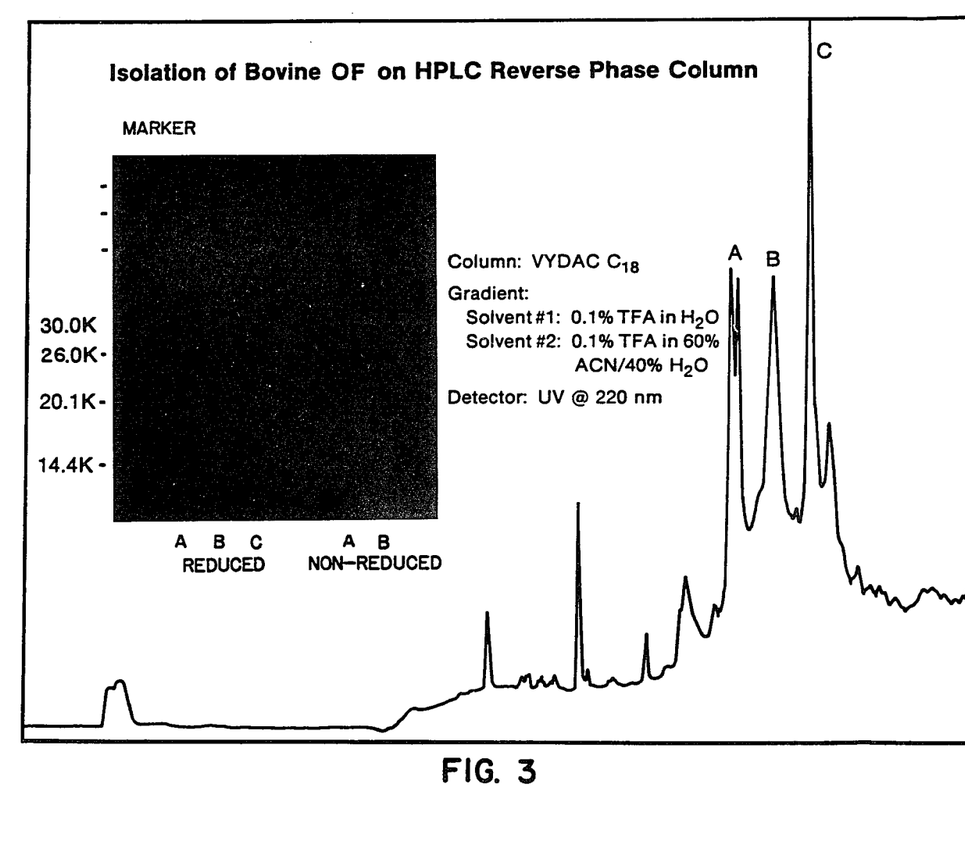
FIG. 3 shows the results according to absorbance and electrophoresis of RP-HPLC conducted on the 100-250 mM NaCl fraction from the CMC column of FIG. 2.

The lyophilized fraction from paragraph C.2 was dissolved in 0.1% trifluoroacetic acid (TFA) and aliquots of this solution loaded onto a Vydac C18 RP-HPLC column (4.6 mm ID×25 cm) and washed with 0.1% TFA for 5 min at 1 ml/min. The eluting solvent was a 0-60% acetonitrile gradient in 0.1% TFA at a rate of 2%/min. Two peaks containing activity were obtained—peak A at about 29.5 min and peak B at about 31.3 min. FIG. 3 shows the absorbance and electrophoretic profiles (reduced and nonreduced) of peaks A and B.

Figure 4:
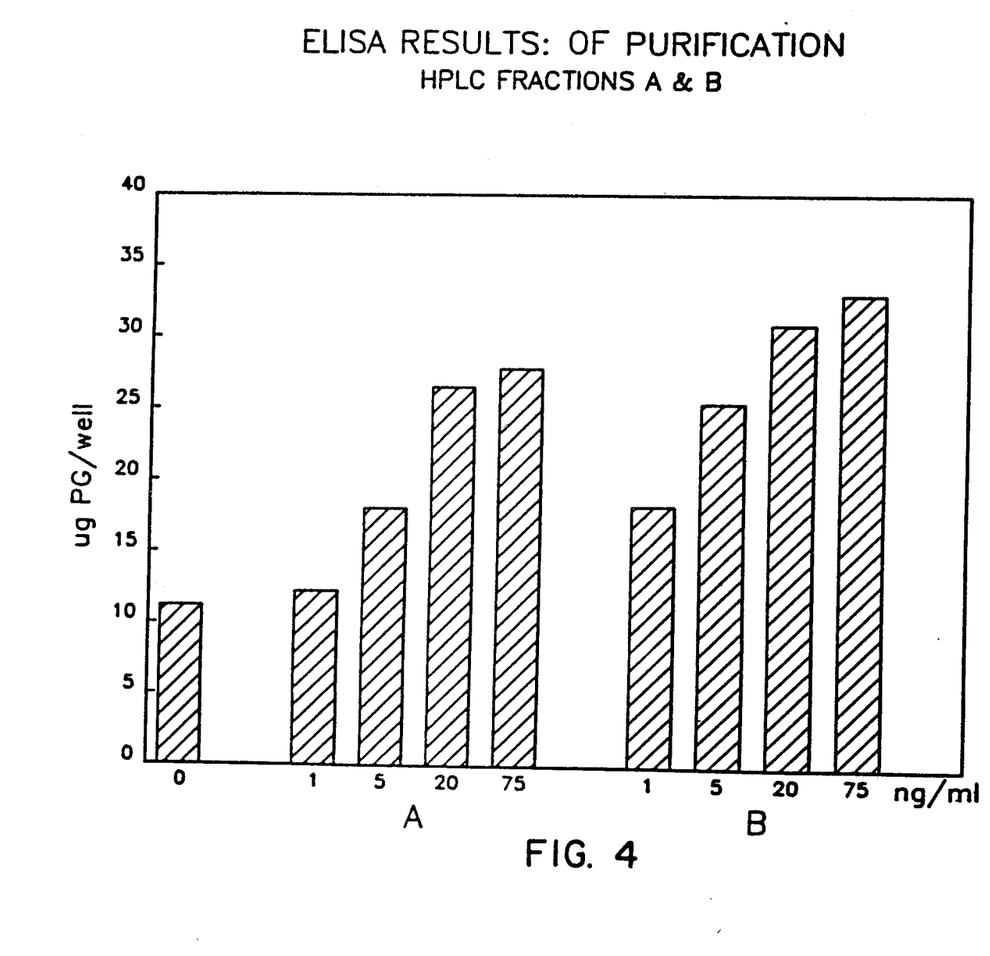
FIG. 4 shows the result of ELISA using the active fractions obtained from RP-HPLC as shown in FIG. 3.

FIG. 4 shows the results of ELISAs run using the purified proteins of peaks A and B at concentrations of 1, 5, 20, and 75 ng/ml. These results show a clear dose response.

C.4. Purification by Gel Electrophoresis

Figure 5:
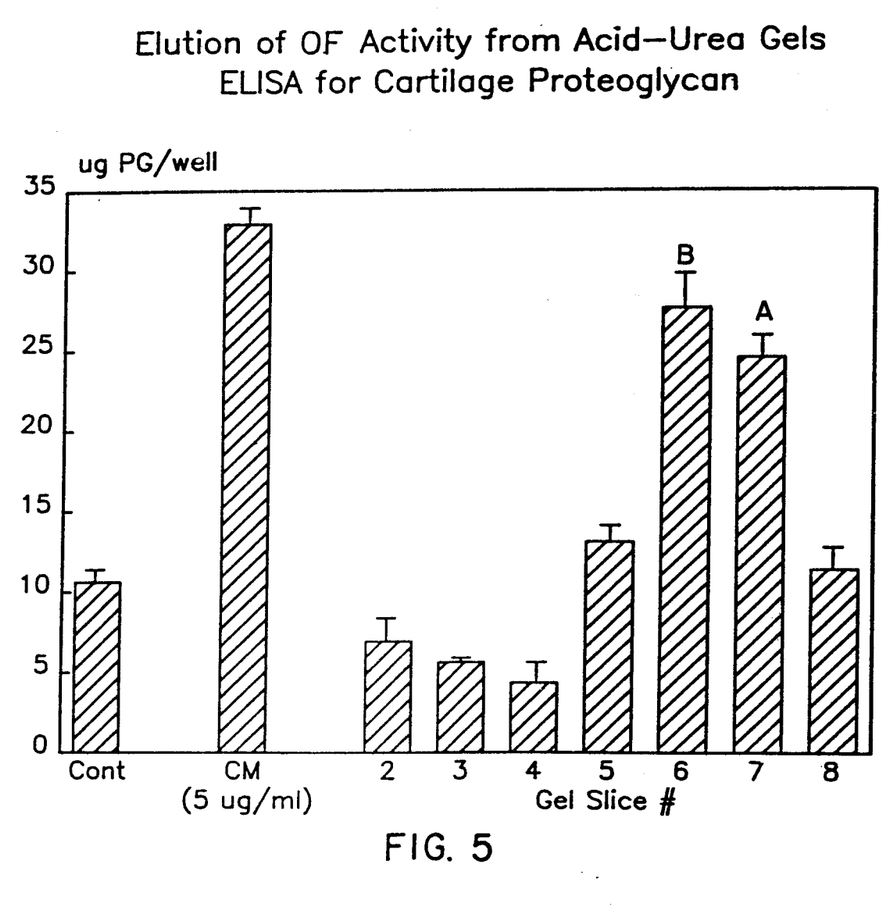
FIG. 5 shows the results of ELISA run on gel fractions obtained from electrophoresis of the 100-250 mM NaCl eluate from CMC shown in FIG. 2.

The lyophilized fraction from paragraph C.2. was fractionated by electrophoresis on an acetic acid-urea gel using the general procedure of Paynim, S. and Chalkley, R., *Arch Bioch Biophys* (1969) 130:337-346. The results of the ELISAs on the gel slices are shown in FIG. 5. These results are comparable to the results on peaks A and B (corresponding to gel slices 7 and 6) of the RP-HPLC.

C.5. Purification by Treatment with Anion Exchange Resin

The fraction F2 from paragraph C.1.c representing low molecular weight proteins was dissolved in buffer containing 6M urea, 20 mM sodium phosphate, pH 7.2, 20 mM NaCl, and protease inhibitors. The solution was then run over a DEAE cellulose column equilibrated with the same buffer. The flow-through fraction, which contains the OF, was dialyzed against water to remove urea, and the OF recovered by lyophilization. Alternatively, the flow-through volume was dialyzed against 0.01 NHCl, and stored in 0.01 NHCl at a protein concentration of 1-10 mg/ml. The foregoing solution was stable over a period of several months.

D. Preparation of Non-fibrillar Collagen

Non-fibrillar collagen may be provided in commercial form by utilizing Zygen ®, collagen in solutions (CIS) which is commercially available. This is an atelopeptide form of solubilized collagen having a pH of approximately 2.

E. Preparation of the Inductive Compositions

E.1. Non-Fibrillar Collagen Only

To prepare a composition containing only non-fibrillar collagen in admixture with the purified OF, CIS at 1-3 mg/ml in 0.01N HCl was mixed with partially purified or highly purified OF (as described in paragraph C above) also dissolved in 0.01N HCl to give an amount of approximately 10 ppm in the final composition, and stirred for 1-2 hr at 4° C. The mixture was dialyzed against water and then lyophilized.

E.2. Non-Fibrillar Collagen Plus BCP

To prepare a composition containing only a small percentage of non-fibrillar collagen, CIS at a concentration of 1-3 mg/ml was mixed with bone collagen powder (BCP) (prepared as described in U.S. Ser. No. 628,328 (supra), incorporated herein by reference) to give a final concentration of collagen contributed by CIS as 5% by weight of total collagen. To this mixture was added OF, partially purified as set forth in paragraph C.5, in an amount sufficient to give 50 ppm as claculated on the basis of purified homogeneous material. This mixture was stirred to 1-2 hr at 4° C., dialyzed against water and lyophilized.

F. Assay of Inductive Implants

F.1. Implantation of Compositions of the Invention

The lyophilized materials prepared in paragraph E.2 were rehydrated in 2 parts by weight of sterile water. The rehydrated materials were made into pellets weighing approximately 80-100 mg wet. The pellets were put into gelatin capsules and the capsules implanted subcutaneously in the ventral thoracic region of male rats. Each rat received two implants of the same material on lateral sides, and explants for testing were removed at 14 and 28 days. The explants were assayed by histology, by assay for alkaline phosphatase activity and for metal ions, and for cartilage proteoglycans.

The sera of the implanted rats were also examined for circulating antibodies against the implants.

F.2. Non-immunogenicity of the Implants

Sera were removed from the implanted animals after 28 days, and assayed for the presence of antibodies against the implanted material using an enzyme linked immunosobent assay (ELISA) technique; Microtiter wells were coated with 2-5 μg of each of the components of the composition in 20 mM carbonate buffer (100 μl) pH 9.6 at 4° C. overnight. The wells were washed 3 times with PBS containing 0.05% Tween 20 surfactant so as to remove unbound antigen. The rat sera were then added for 2 hr at room temperature, and the wells washed 3 times with PBS-Tween 20 surfactant. Goat anti-rat IgG conjugated with horseradish peroxidase (1:2000 dilution) was added, and the wells incubated for 1.5-2 hr at room temperature. Unbound labeled antibody was then removed with PBS-Tween 20 with surfactant, and peroxidase substrate was added.

The plates were incubated at room temperature for 30 min, and the plates then scanned for optical density.

Antibodies were not detected in any of the rats whose sera were tested, even using undiluted sera. Controls consisted of sera from rats injected with crude extract from DMB (i.e. unfractionated material prepared as set forth in paragraph C.1.b.) which were positive in the ELISA technique used, and gave high antibody titers.

F.3. Characterization of Explants-Histology

Explants which had been removed after 7, 14, and 28 days were subjected to histological assessment by fixing in 10% neutral formalin for 26 hr, and then processing for paraffin embedding. 4-6 micron sections were taken from the imbedded tissues and were subsequently stained with either hematoxylin-eosin or with Saphranin-O. Saphranin-O is selective for cartilage proteoglycan. All of the explanted material indicated the presence of cartilage proteoglycan by this technique.

F.4. Assay for Extractable Bone Components 6 rats were implanted with the OF-containing matrix prepared in paragraph E.2, and, as negative controls, 6 rats were implanted with a similar matrix which did not contain OF. Explants were removed after 14 and 28 days. The 14-day explants were extracted prior to analysis for proteoglycan, and for alkaline phosphatase as set forth below; the 28 day explants were used for determination of calcium ion.

F.4.a. Formation of Proteoglycan

Cartilage proteoglycan was assayed by an ELISA technique. The explants were weighed immediately after removal and frozen at $-70°$ C. until extraction. For the extraction, the explants were cut into slices, and homogenized in ice cold extraction buffer in a Tekmar Tissuemizer for two 30 sec bursts at maximum setting. The extraction buffer was 6M guanidine hydrochloride, 75 mM sodium acetate or 4M guanidine hydrochloride, 50 mM acetate both containing 20 mM EDTA, 1 mM PMSF and 10 mM NEM at pH 5.8. Buffer was used in a volume equal to the weight of the explant extracted, and the samples were incubated overnight (20 hr) at 4° C. The samples were then centrifuged at 12,000 rpm for 1 hr at 4° C., and the supernatants dialyzed overnight at 4° C. against 50 volumes of 50 mM Tris, 200 mM NaCl, pH 7.4. The dialyzate was subjected to ELISA performed as described by Rennard, et al, *Arch Biochem Biophys* (1980) 207:399 and by Seyedin, S., et al, *J. Cell Biol* (1983) 97:1950 using polystyrene microplates (Flow Laboratories, McClean, Va.). The antisera and the proteoglycan standard were prepared from Swarm rat chondrosarcoma tissue as described by Seyedin, S., et al, (supra). Horseradish peroxidase conjugated goat anti-rabbit IgG was used as the second antibody, samples were assayed in different solutions in PBS 0.05%, Tween 20, 1 mg/ml BSA and quantitated by use of the inhibition ELISA described by Shuures, et al, *Clin Chim* (1977) 81:1.

Explants which had contained OF showed a proteoglycan content of 490±30 mg/g wet tissue; explants which had contained no OF showed only 35±5 mg/g wet tissue.

F.4.b. Extractable Calcium

The formation of bone was also assessed by determination of calcium. The explants were cut in small pieces and suspended in 1:10 (m/w) and 1:20 (m/v) of 0.5N HCl to dissolve the ions. The samples were incubated for another 5 days at room temperature and centrifuged at 12,000 rpm for 40 min. The calcium concentration of the supernatant was determined by atomic adsorption (Trace Analysis Laboratory, Hayward, Calif.); and found to be 30±5 mg/g wet tissue.

F.4.c. Analysis for Alkaline Phosphatase

To determine alkaline phosphatase (AP), the explants were cut in small pieces and homogenized in 3 ml ice cold 1.5M NaCl, 3 mM NaHCO$_3$, pH 7.5. The homogenized samples were then centrifuged at 12,000 rpm for 50 min at 4° C., and an aliquot of the supernatant diluted 1:10 in cold distilled water. The method of Huggins, et al, *J Exp Med* (1961) 114:761 was used to assess alkaline phosphatase using polystyrene plates. Explants which had orginally contained OF showed 17±5 units of AP per gram of wet tissue, explants which contained no OF showed no AP activity.

We claim:

1. A hypoimmunogenic composition suitable for implantation to effect bone repair in a vertebrate which comprises an osteoinductively effective amount of a protein osteoinductive factor (OF) derived from bone, which OF is sufficiently pure to be hypoimmunogenic in a xenogeneic host in admixture with a carrier which is hypoimmunogenic in a xenogeneic host containing at least 5% by weight of non-fibrillar collagen.

2. The composition of claim 1 wherein the OF comprises between about 1 ppm and 1000 ppm of the implant.

3. The composition of claim 1 wherein the carrier contains at least 10% by weight of non-fibrillar collagen.

4. The composition of claim 1 wherein the non-fibrillar collagen is atelopeptide collagen.

5. The composition of claim 1 wherein the non-fibrillar collagen is provided as collagen in solution.

6. The composition of claim 1 wherein the carrier contains bone collagen powder in an amount not exceeding 95%.

7. The composition of claim 1 wherein the carrier contains hydroxyapatite in an amount not exceeding 95%.

8. The composition of claim 1 wherein the carrier contains a mixture of bone collagen powder and hydroxyapatite in a total amount not exceeding 95%.

9. The composition of claim 1 wherein the OF is prepared by a process which includes treating a chaotropic extract of bone with a molecular sieve to isolate a fraction of molecular weight of less than 30,000.

10. The composition of claim 9 wherein the OF is further purified by treating with DEAE cellulose and utilizing the unbound fraction.

11. The composition of claim 9 wherein the OF is further purified by absorbing said fraction to a cation exchange resin and recovering the factor.

12. The composition of claim 11 wherein the OF is further purified by HPLC.

13. The composition of claim 11 wherein the OF is further purified by gel electrophoresis.

14. A method of effecting bone repair in vertebrates which comprises implanting into a bone defect a composition hypoimmunogenic in a xenogeneic host which comprises an osteoinductively effective amount of a protein osteoinductive factor (OF) derived from bone, which OF is sufficiently pure to be hypoimmunogenic in a xenogeneic host, in admixture with a carrier which is hypoimmunogenic in a xenogeneic host containing at least 5% by weight of non-fibrillar collagen.

* * * * *